US012629279B2

(12) United States Patent
Gliner et al.

(10) Patent No.: US 12,629,279 B2
(45) Date of Patent: *May 19, 2026

(54) MULTI-CHANNEL PIEZOELECTRIC RESONANT SYSTEM

(71) Applicant: JOHNSON & JOHNSON SURGICAL VISION, INC., Irvine, CA (US)

(72) Inventors: Vadim Gliner, Haifa (IL); Assaf Govari, Haifa (IL); Christopher Thomas Beeckler, Brea, CA (US); Joseph Thomas Keyes, Sierra Madre, CA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 601 days.

This patent is subject to a terminal disclaimer.

(21) Appl. No.: 17/547,545

(22) Filed: Dec. 10, 2021

(65) Prior Publication Data

US 2022/0096269 A1     Mar. 31, 2022

Related U.S. Application Data

(63) Continuation-in-part of application No. 17/324,576, filed on May 19, 2021, now Pat. No. 12,472,094, and
(Continued)

(51) Int. Cl.
*A61F 9/007*       (2006.01)
*B06B 1/02*        (2006.01)

(52) U.S. Cl.
CPC ........ *A61F 9/00745* (2013.01); *B06B 1/0207* (2013.01); *B06B 2201/76* (2013.01)

(58) Field of Classification Search
CPC ............... A61F 9/00745; B06B 1/0207; B06B 2201/76
See application file for complete search history.

(56) References Cited

U.S. PATENT DOCUMENTS 2,434,480 A     1/1948   Anderson
2,763,840 A     9/1956   Pfleger
                  (Continued)

FOREIGN PATENT DOCUMENTS

CA       2242328 A1    5/1998
CN     109029690 A    12/2018
                  (Continued)

OTHER PUBLICATIONS

U.S. Appl. No. 17/231,450, titled "Compensating for Imperfect Behavior of Multi-Piezoelectric Crystal," filed Apr. 15, 2021.
(Continued)

*Primary Examiner* — Andrew Restaino

(57) ABSTRACT

A phacoemulsification system includes a phacoemulsification probe and one or more signal generators. The phacoemulsification probe includes (i) a piezoelectric actuator, (ii) a segmented electrode, including multiple electrode segments attached to respective angular sections of a face of the piezoelectric actuator, (iii) a common ground electrode attached to the piezoelectric actuator, and (iv) a needle configured to be inserted into a lens capsule of an eye and to be vibrated by the piezoelectric actuator. The one or more signal generators are configured to vibrate the piezoelectric actuator by applying multiple drive signals between the multiple respective electrode segments and the common ground electrode.

12 Claims, 5 Drawing Sheets

Related U.S. Application Data a continuation-in-part of application No. 16/856,835, filed on Apr. 23, 2020.

(56) References Cited

U.S. PATENT DOCUMENTS

| | | | |
|---|---|---|---|
| 2,838,696 A * | 6/1958 | Thurston | G01H 1/10 |
| | | | 318/116 |
| 3,469,213 A | 9/1969 | Leonard | |
| 3,857,387 A | 12/1974 | Shock | |
| 3,885,569 A | 5/1975 | Judson | |
| 3,941,122 A | 3/1976 | Jones | |
| 4,012,647 A | 3/1977 | Balamuth et al. | |
| 4,063,557 A | 12/1977 | Wuchinich et al. | |
| 4,092,986 A | 6/1978 | Schneiderman | |
| 4,156,187 A | 5/1979 | Brumbach et al. | |
| 4,184,510 A | 1/1980 | Murry et al. | |
| 4,199,246 A | 4/1980 | Muggli | |
| 4,223,676 A | 9/1980 | Wuchinich et al. | |
| 4,343,111 A | 8/1982 | Inoue | |
| 4,378,538 A | 3/1983 | Gignoux | |
| 4,469,098 A | 9/1984 | Davi | |
| 4,520,818 A | 6/1985 | Mickiewicz | |
| 4,736,130 A | 4/1988 | Puskas | |
| 4,750,902 A * | 6/1988 | Wuchinich | A61M 1/79 |
| | | | 604/27 |
| 4,808,948 A | 2/1989 | Patel et al. | |
| 4,827,911 A | 5/1989 | Broadwin et al. | |
| 4,861,332 A | 8/1989 | Parisi | |
| 4,886,060 A | 12/1989 | Wiksell | |
| 4,903,696 A | 2/1990 | Stasz et al. | |
| 4,952,834 A | 8/1990 | Okada | |
| 4,954,960 A | 9/1990 | Lo et al. | |
| 4,970,656 A | 11/1990 | Lo et al. | |
| 4,983,901 A | 1/1991 | Lehmer | |
| 5,001,649 A | 3/1991 | Lo et al. | |
| 5,019,794 A | 5/1991 | Letessier et al. | |
| 5,091,656 A | 2/1992 | Gahn | |
| 5,126,589 A | 6/1992 | Renger | |
| 5,162,044 A | 11/1992 | Gahn et al. | |
| 5,162,759 A | 11/1992 | Yajima | |
| 5,209,221 A | 5/1993 | Riedlinger | |
| 5,213,569 A | 5/1993 | Davis | |
| 5,242,404 A | 9/1993 | Conley et al. | |
| 5,249,121 A | 9/1993 | Baum et al. | |
| 5,268,624 A | 12/1993 | Zanger | |
| 5,279,547 A | 1/1994 | Costin | |
| 5,285,127 A | 2/1994 | Egley et al. | |
| 5,318,563 A | 6/1994 | Malis et al. | |
| 5,331,951 A | 7/1994 | Kepley | |
| 5,342,293 A | 8/1994 | Zanger | |
| 5,370,602 A | 12/1994 | Kepley | |
| 5,388,569 A | 2/1995 | Kepley | |
| 5,403,307 A | 4/1995 | Zelman | |
| 5,405,614 A | 4/1995 | D'Angelo et al. | |
| 5,406,503 A | 4/1995 | Williams, Jr. et al. | |
| 5,417,246 A | 5/1995 | Perkins et al. | |
| 5,431,663 A | 7/1995 | Carter | |
| 5,431,664 A | 7/1995 | Ureche et al. | |
| 5,451,161 A | 9/1995 | Sharp | |
| 5,453,087 A | 9/1995 | Malinowski | |
| 5,520,633 A | 5/1996 | Costin | |
| 5,523,058 A | 6/1996 | Umemura et al. | |
| 5,534,741 A | 7/1996 | Smith | |
| 5,547,459 A | 8/1996 | Kaufman et al. | |
| 5,549,632 A | 8/1996 | Lai | |
| 5,582,578 A | 12/1996 | Zhong et al. | |
| 5,591,127 A | 1/1997 | Barwick, Jr. et al. | |
| 5,700,240 A | 12/1997 | Barwick, Jr. et al. | |
| 5,733,256 A | 3/1998 | Costin | |
| 5,738,677 A | 4/1998 | Colvard et al. | |
| 5,766,146 A | 6/1998 | Barwick, Jr. | |
| 5,797,494 A | 8/1998 | Balling et al. | |
| 5,800,365 A | 9/1998 | Zhong et al. | |
| 5,808,396 A | 9/1998 | Boukhny | |

| | | | |
|---|---|---|---|
| 5,814,922 A * | 9/1998 | Uchino | H10N 30/40 |
| | | | 310/366 |
| 5,825,164 A | 10/1998 | Williams et al. | |
| 5,836,959 A | 11/1998 | Seibel et al. | |
| 5,843,109 A | 12/1998 | Mehta et al. | |
| 5,852,794 A | 12/1998 | Staggs | |
| 5,873,885 A | 2/1999 | Weidenbenner | |
| 5,897,569 A | 4/1999 | Kellogg et al. | |
| 5,938,677 A | 8/1999 | Boukhny et al. | |
| 5,971,980 A | 10/1999 | Sherman | |
| 5,979,494 A | 11/1999 | Perkins et al. | |
| 5,984,882 A | 11/1999 | Rosenschein et al. | |
| 5,997,528 A | 12/1999 | Bisch et al. | |
| 6,010,496 A | 1/2000 | Appelbaum et al. | |
| 6,027,515 A | 2/2000 | Cimino | |
| 6,028,387 A | 2/2000 | Boukhny | |
| 6,053,906 A | 4/2000 | Honda et al. | |
| 6,083,193 A | 7/2000 | Kadziauskas et al. | |
| 6,086,598 A | 7/2000 | Appelbaum et al. | |
| 6,117,126 A | 9/2000 | Appelbaum et al. | |
| 6,155,975 A | 12/2000 | Urich et al. | |
| 6,161,545 A | 12/2000 | Chow | |
| 6,174,309 B1 | 1/2001 | Wrublewski et al. | |
| 6,175,180 B1 | 1/2001 | Angelini et al. | |
| 6,193,683 B1 | 2/2001 | Ludin et al. | |
| 6,203,516 B1 | 3/2001 | Kepley | |
| 6,251,113 B1 | 6/2001 | Appelbaum et al. | |
| 6,261,297 B1 | 7/2001 | Kadziauskas et al. | |
| 6,274,963 B1 * | 8/2001 | Estabrook | A61B 17/320068 |
| | | | 310/316.02 |
| 6,319,220 B1 | 11/2001 | Bylsma | |
| 6,346,764 B1 * | 2/2002 | Boyd | H10N 30/40 |
| | | | 310/366 |
| 6,391,020 B1 | 5/2002 | Kurtz et al. | |
| 6,391,042 B1 | 5/2002 | Cimino | |
| 6,394,974 B1 | 5/2002 | Kadziauskas et al. | |
| 6,402,769 B1 | 6/2002 | Boukhny | |
| 6,425,883 B1 | 7/2002 | Urich et al. | |
| 6,428,531 B1 | 8/2002 | Msuri et al. | |
| 6,443,900 B2 | 9/2002 | Adachi et al. | |
| 6,452,120 B1 | 9/2002 | Chen | |
| 6,452,123 B1 | 9/2002 | Chen | |
| 6,452,883 B2 | 9/2002 | Chan | |
| 6,487,447 B1 | 11/2002 | Weimann et al. | |
| 6,506,176 B1 | 1/2003 | Mittelstein et al. | |
| 6,588,277 B2 | 7/2003 | Giordano et al. | |
| 6,589,204 B1 | 7/2003 | Sussman et al. | |
| 6,610,052 B2 | 8/2003 | Furumoto | |
| 6,629,948 B2 | 10/2003 | Rockley et al. | |
| 6,632,193 B1 | 10/2003 | Davison et al. | |
| 6,699,212 B1 | 3/2004 | Kadziauskas et al. | |
| 6,726,679 B1 | 4/2004 | Dick et al. | |
| 6,733,491 B2 | 5/2004 | Kadziauskas et al. | |
| 6,780,165 B2 | 8/2004 | Kadziauskas et al. | |
| 6,808,396 B2 | 10/2004 | Kawaguchi et al. | |
| 6,852,092 B2 | 2/2005 | Kadziauskas et al. | |
| 6,884,252 B1 | 4/2005 | Urich et al. | |
| 6,890,332 B2 | 5/2005 | Truckai et al. | |
| 6,896,674 B1 | 5/2005 | Woloszko et al. | |
| 6,908,472 B2 | 6/2005 | Wiener et al. | |
| 6,939,317 B2 | 9/2005 | Zacharias | |
| 6,945,981 B2 | 9/2005 | Donofrio et al. | |
| 6,962,583 B2 | 11/2005 | Kadziauskas et al. | |
| 6,997,935 B2 | 2/2006 | Anderson et al. | |
| 7,077,820 B1 | 7/2006 | Kadziauskas et al. | |
| 7,169,123 B2 * | 1/2007 | Kadziauskas | B06B 1/0253 |
| | | | 606/107 |
| 7,193,521 B2 | 3/2007 | Moberg et al. | |
| 7,316,664 B2 | 1/2008 | Kadziauskas et al. | |
| 7,485,106 B2 | 2/2009 | Kadziauskas et al. | |
| 7,671,693 B2 | 3/2010 | Brobston et al. | |
| 7,785,336 B2 | 8/2010 | Staggs | |
| 7,857,783 B2 | 12/2010 | Kadziauskas et al. | |
| 7,938,120 B2 | 5/2011 | Kadziauskas et al. | |
| 7,998,156 B2 | 8/2011 | Staggs | |
| 8,020,565 B2 | 9/2011 | Kadziauskas et al. | |
| 8,034,067 B2 | 10/2011 | Staggs | |
| 8,195,286 B2 | 6/2012 | Kadziauskas et al. | |
| 8,197,436 B2 | 6/2012 | Kadziauskas et al. | |

(56)                References Cited

U.S. PATENT DOCUMENTS

| | | |
|---|---|---|
| 8,202,287 B2 | 6/2012 | Staggs |
| 8,231,564 B2 | 7/2012 | Kadziauskas et al. |
| 8,303,613 B2 | 11/2012 | Crandall et al. |
| 8,366,728 B2 | 2/2013 | Staggs |
| 8,545,528 B2 | 10/2013 | Rob et al. |
| 8,623,040 B2 | 1/2014 | Artsyukhovich et al. |
| 8,852,138 B2 | 10/2014 | Kadzlauskas et al. |
| 8,876,747 B2 | 11/2014 | Kadziauskas et al. |
| 8,887,735 B2 | 11/2014 | Kadzlauskas et al. |
| 8,945,162 B2 | 2/2015 | Kadziauskas et al. |
| 9,018,887 B2 | 4/2015 | Paschke |
| 9,226,849 B2 | 1/2016 | Staggs |
| 9,572,711 B2 | 2/2017 | Raney et al. |
| 9,642,745 B2 | 5/2017 | Kadziauskas et al. |
| 9,707,127 B2 | 7/2017 | Kadziauskas |
| 9,788,998 B2 | 10/2017 | Kadziauskas et al. |
| 10,245,179 B2 | 4/2019 | Kadziauskas et al. |
| 10,363,166 B2 | 7/2019 | Raney |
| 10,478,337 B2 | 11/2019 | Greenbaum et al. |
| 2001/0003155 A1 | 6/2001 | Rockley et al. |
| 2001/0003295 A1 | 6/2001 | Langlotz et al. |
| 2001/0003385 A1 | 6/2001 | Ise |
| 2001/0039389 A1 | 11/2001 | Sakurai et al. |
| 2001/0048356 A1 | 12/2001 | Owen et al. |
| 2002/0010477 A1 | 1/2002 | Hirt et al. |
| 2002/0052600 A1 | 5/2002 | Davison et al. |
| 2002/0072741 A1 | 6/2002 | Sliwa et al. |
| 2002/0082793 A1 | 6/2002 | Kadziauskas et al. |
| 2002/0173814 A1 | 11/2002 | Jung et al. |
| 2003/0047434 A1 | 3/2003 | Hanson et al. |
| 2004/0092921 A1 | 5/2004 | Kadziauskas et al. |
| 2004/0092922 A1 | 5/2004 | Kadziauskas et al. |
| 2004/0193182 A1 | 9/2004 | Yaguchi et al. |
| 2004/0215127 A1 | 10/2004 | Kadziauskas et al. |
| 2005/0054971 A1 | 3/2005 | Steen et al. |
| 2005/0209560 A1 | 9/2005 | Boukhny et al. |
| 2005/0209621 A1 | 9/2005 | Gordon et al. |
| 2005/0288665 A1 | 12/2005 | Woloszko |
| 2006/0036180 A1 | 2/2006 | Boukhny et al. |
| 2006/0079788 A1 | 4/2006 | Anderson et al. |
| 2006/0149301 A1 | 7/2006 | Claus |
| 2006/0195077 A1 | 8/2006 | Kadziauskas et al. |
| 2006/0264809 A1 | 11/2006 | Hansmann et al. |
| 2007/0056596 A1 | 3/2007 | Fanney et al. |
| 2007/0066978 A1 | 3/2007 | Schafer et al. |
| 2007/0073214 A1 | 3/2007 | Dacquay et al. |
| 2007/0078379 A1 | 4/2007 | Boukhny et al. |
| 2007/0249941 A1 | 10/2007 | Salehi et al. |
| 2008/0033342 A1 | 2/2008 | Staggs |
| 2008/0139994 A1 | 6/2008 | Mackool et al. |
| 2008/0146989 A1 | 6/2008 | Zacharias |
| 2008/0154255 A1 | 6/2008 | Panos et al. |
| 2008/0294087 A1 | 11/2008 | Steen et al. |
| 2008/0319374 A1 | 12/2008 | Zacharias |
| 2009/0005712 A1 | 1/2009 | Raney |
| 2010/0069825 A1 | 3/2010 | Raney |
| 2010/0125292 A1 | 5/2010 | Wiener et al. |
| 2010/0185150 A1 | 7/2010 | Zacharias |
| 2011/0092886 A1 | 4/2011 | Raney et al. |
| 2011/0196403 A1 | 8/2011 | Robertson et al. |
| 2011/0196404 A1 | 8/2011 | Dietz et al. |
| 2012/0029353 A1 | 2/2012 | Slayton et al. |
| 2013/0006265 A1 | 1/2013 | Crandall et al. |
| 2013/0006266 A1* | 1/2013 | Crandall ............. A61F 9/00745 |
| | | 606/128 |
| 2013/0057253 A1 | 3/2013 | Jacobson |
| 2013/0314077 A1 | 11/2013 | Okada et al. |
| 2013/0331872 A1 | 12/2013 | Parham et al. |
| 2014/0024969 A1 | 1/2014 | Govari et al. |
| 2014/0074013 A1 | 3/2014 | McCary et al. |
| 2014/0180128 A1 | 6/2014 | Corl |

| | | |
|---|---|---|
| 2015/0148712 A1 | 5/2015 | Loven et al. |
| 2017/0312129 A1 | 11/2017 | Kadziauskas et al. |
| 2018/0056328 A1 | 3/2018 | Downey et al. |
| 2018/0234773 A1 | 8/2018 | Kaplan et al. |
| 2021/0196513 A1 | 7/2021 | Govari et al. |
| 2021/0330493 A1 | 10/2021 | Steen et al. |
| 2021/0361481 A1 | 11/2021 | Gliner et al. |
| 2022/0331159 A1 | 10/2022 | Gliner |

FOREIGN PATENT DOCUMENTS

| | | |
|---|---|---|
| DE | 232755 A1 | 2/1986 |
| DE | 3910200 A1 | 10/1990 |
| DE | 19940712 A1 | 3/2001 |
| EP | 0270819 A2 | 6/1988 |
| EP | 0336620 A2 | 10/1989 |
| EP | 336620 B1 | 12/1993 |
| EP | 0945732 A2 | 9/1999 |
| EP | 1351631 A1 | 10/2003 |
| EP | 0955984 B1 | 4/2004 |
| EP | 1537840 A1 | 6/2005 |
| EP | 1608280 A2 | 12/2005 |
| EP | 1625836 A1 | 2/2006 |
| EP | 1849444 A1 | 10/2007 |
| JP | 63315049 A | 12/1988 |
| JP | 2204337 A2 | 8/1990 |
| JP | 5038343 A2 | 2/1993 |
| JP | 6183762 A2 | 7/1994 |
| JP | 6189972 A2 | 7/1994 |
| JP | 9313496 A2 | 12/1997 |
| JP | 2001161740 A | 6/2001 |
| JP | 2002087836 A2 | 3/2002 |
| JP | 2002233534 A2 | 8/2002 |
| WO | 9211814 A1 | 7/1992 |
| WO | 9520374 A1 | 8/1995 |
| WO | 9808442 A1 | 3/1998 |
| WO | 0000298 A1 | 1/2000 |
| WO | 0051508 A1 | 9/2000 |
| WO | 0064388 A1 | 11/2000 |
| WO | 0113838 A1 | 3/2001 |
| WO | 0152782 A1 | 7/2001 |
| WO | 02056806 A1 | 7/2002 |
| WO | 2005037156 A1 | 4/2005 |
| WO | 05092023 A2 | 10/2005 |
| WO | 2008016870 A3 | 2/2008 |
| WO | 2013173495 A1 | 11/2013 |
| WO | 2018022968 A1 | 2/2018 |
| WO | 2023105323 A1 | 6/2023 |

OTHER PUBLICATIONS

DAVIS P.L., et al., "Cavitating Microbubbles Create Shock Waves that Emulsify Cataract," in: The Art of Phacoemulsification, Mehta K.R., et al., eds., Jaypee Brothers, New Delhi, 2001, pp. 45-50.

Devine M.T., ed., "How to Set the Dials," in: Phacoemulsification Surgery, Pergamon Press, Chapter 2, 1991, pp. 7-28.

Ocusystem Operation Manual, May 1995, 79 pages.

Ophthalmology Times, Pulsar Cuts Phaco Time, Boosts Efficiency in Cataract Removal, Aug. 15, 1986, vol. 11 (16), Harcourt Brace Jovanovich, Inc., 1 page.

Pacifico R.L., "Ultrasonic Energy in Phacoemulsification: Mechanical Cutting and Cavitation," Journal of Cataract & Refractive Surgery, 1994, vol. 20 (3), pp. 338-341.

Taylor W.F., et al., "Intraoperative Troubleshooting of an Advanced Phacoemulsification System," The Surgial Technologist, 1985, vol. 17 (2), pp. 11-14.

U.S. Appl. No. 16/704,054, filed Dec. 5, 2019, titled "Phacoemulsification Apparatus".

Geuder, "Opthalmic Surgical System Megatron S3", Operating Instructions Version 2.1, 118 pages, 2002.

* cited by examiner

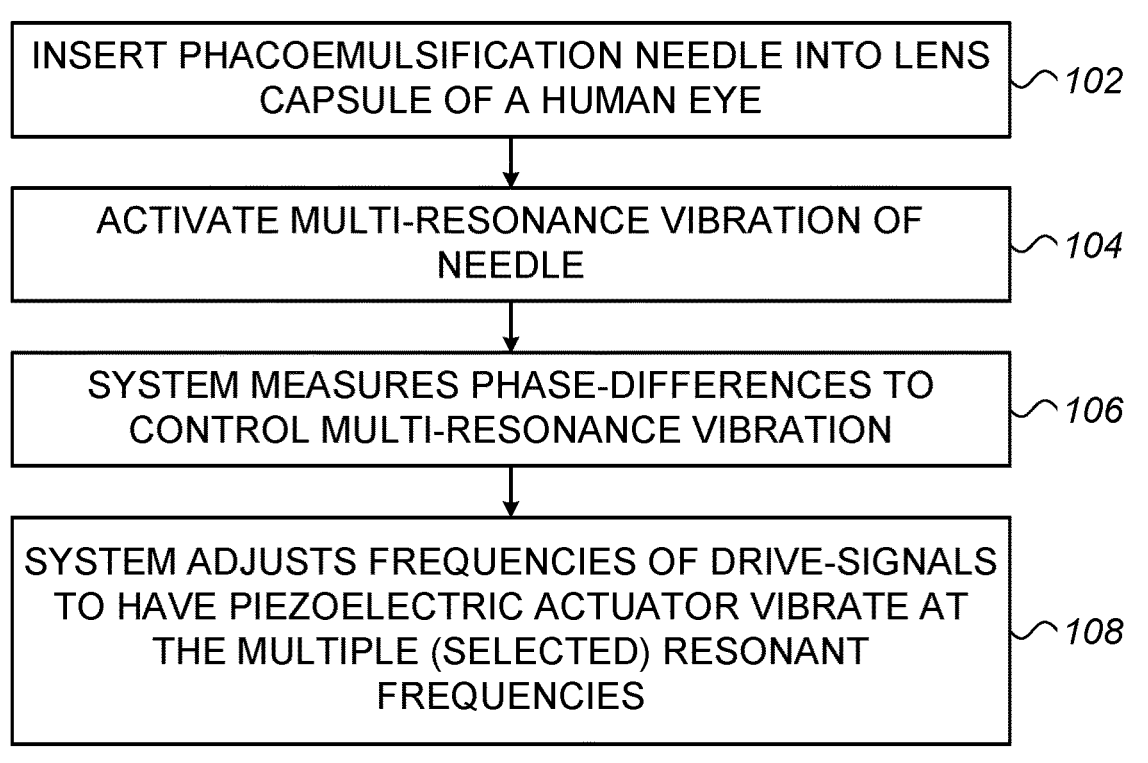
| | |
|---|---|
| INSERT PHACOEMULSIFICATION NEEDLE INTO LENS CAPSULE OF A HUMAN EYE | 102 |
| ACTIVATE MULTI-RESONANCE VIBRATION OF NEEDLE | 104 |
| SYSTEM MEASURES PHASE-DIFFERENCES TO CONTROL MULTI-RESONANCE VIBRATION | 106 |
| SYSTEM ADJUSTS FREQUENCIES OF DRIVE-SIGNALS TO HAVE PIEZOELECTRIC ACTUATOR VIBRATE AT THE MULTIPLE (SELECTED) RESONANT FREQUENCIES | 108 |
*FIG. 3*
*FIG. 4*
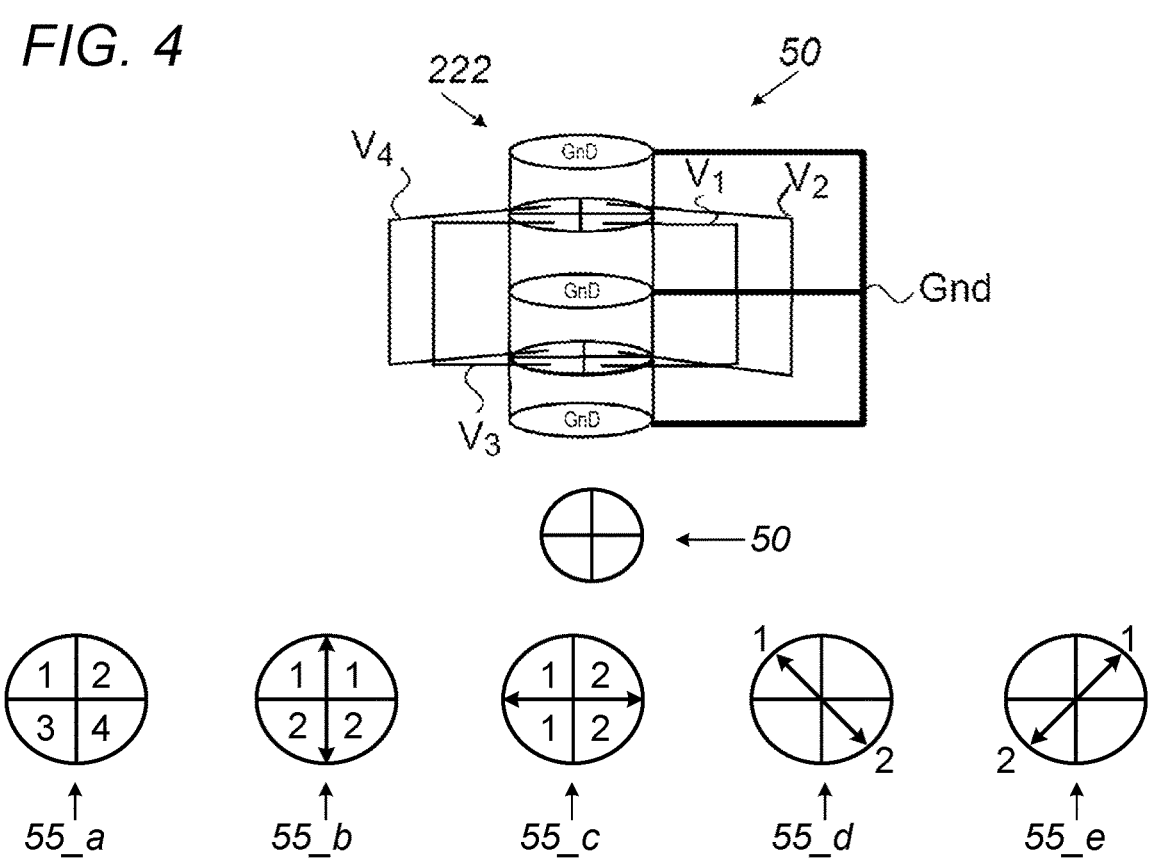

MULTI-CHANNEL PIEZOELECTRIC RESONANT SYSTEM

CROSS-REFERENCE TO RELATED APPLICATIONS

The present application is a continuation-in-part of U.S. patent application Ser. No. 16/856,835, titled "Multi-Channel Piezoelectric Resonant System," filed Apr. 23, 2020, and of U.S. patent application Ser. No. 17/324,576 titled "Phacoemulsification Probe Comprising Magnetic Sensors and/or Multiple Independent Piezoelectric Vibrators," filed May 19, 2021, both whose disclosures are incorporated herein by reference.

FIELD OF THE DISCLOSURE

The present disclosure relates generally to piezoelectric-vibration-based systems, and particularly to phacoemulsification systems.

BACKGROUND OF THE DISCLOSURE

A cataract is a clouding and hardening of the eye's natural lens, a structure which is positioned behind the cornea, iris and pupil. The lens is mostly made up of water and protein and as people age these proteins change and may begin to clump together obscuring portions of the lens. To correct this, a physician may recommend phacoemulsification cataract surgery. In the procedure, the surgeon makes a small incision in the sclera or cornea of the eye. Then a portion of the anterior surface of the lens capsule is removed to gain access to the cataract. The surgeon then uses a phacoemulsification probe, which has an ultrasonic handpiece with a needle. The tip of the needle vibrates at ultrasonic frequency to sculpt and emulsify the cataract while a pump aspirates particles and fluid from the eye through the tip. Aspirated fluids are replaced with irrigation of a balanced salt solution to maintain the anterior chamber of the eye. After removing the cataract with phacoemulsification, the softer outer lens cortex is removed with suction. An intraocular lens (IOL) is then introduced into the empty lens capsule restoring the patient's vision.

Various techniques to vibrate a phacoemulsification needle of a probe were proposed in the patent literature. For example, U.S. Patent Application Publication 2010/0069825 describes a method and system for use in an ocular surgical procedure. The design includes a handpiece having an ultrasonically vibrating tip operational within a plurality of operating modes including a first operating mode and a sensing device, such as a vacuum pressure sensor. A controller is connected to the handpiece and sensing device and is configured to receive data from the sensing device and adjust at least one operational parameter (time/duty cycle of operation, power during operation) associated with the first operating mode and adjust at least one parameter associated with another operating mode based on the data received from the sensing device. Operational modes may include multiple longitudinal or non-longitudinal modes (torsional, transversal, etc.) or combinations of longitudinal and/or non-longitudinal modes.

As another example, U.S. Pat. No. 8,303,613 describes a Langevin transducer horn that uses split electroding or selective electroding of transducer elements and phase relationships of the voltages applied thereto to determine the relative longitudinal and flexural/transverse motion induced in the tip of the horn. In an example, an ultrasonic surgical instrument is provided, that includes a piezoelectric transducer element attached to the horn such that excitation of the piezoelectric element using one of the above electroding causes vibration of a working member of the horn.

U.S. Patent Application Publication 2008/0294087 describes phacoemulsification systems and methods, and more particularly systems and methods for providing transverse phacoemulsification. In accordance with one example, a phacoemulsification system is provided having a handpiece with a needle, wherein the phacoemulsification system is configured to vibrate the needle in both an effective transverse direction and an effective longitudinal direction when power having a single effective operating frequency is applied to the handpiece.

U.S. Pat. No. 8,623,040 describes a phacoemulsification cutting tip with a straight shaft and an angled portion off of the straight shaft that may include a hook on the angled portion to move an axis of rotation of the cutting tip closer to alignment with an extended centerline of the shaft. The cutting tip may be configured to torsionally rotate back and forth on an axis perpendicular to a centerline of the shaft (e.g., rotation around a y-axis). In some examples, lateral vibrations (e.g., side to side along an x-axis or z-axis perpendicular to the y-axis) that result from torsional rotation around the y-axis in a cutting tip without the hook may be reduced through use of the hook to balance the otherwise eccentrically weighted hook. In some examples, the cutting tip may be ultrasonically torsionally vibrated along a small arc (e.g., +/− 5 degrees). The torsional vibrations of the cutting tip may result in lateral motions in the shaft and the cutting tip.

SUMMARY OF THE DISCLOSURE

An example of the present disclosure that is described hereinafter provides a phacoemulsification system including a phacoemulsification probe and one or more signal generators. The phacoemulsification probe includes (i) a piezoelectric actuator, (ii) a segmented electrode, including multiple electrode segments attached to respective angular sections of a face of the piezoelectric actuator, (iii) a common ground electrode attached to the piezoelectric actuator, and (iv) a needle configured to be inserted into a lens capsule of an eye and to be vibrated by the piezoelectric actuator. The one or more signal generators are configured to vibrate the piezoelectric actuator by applying multiple drive signals between the multiple respective electrode segments and the common ground electrode.

In some examples, the one or more signal generators are configured to apply a same drive signal to at least two of the electrode segments.

In other examples, the one or more signal generators are configured to apply different drive signals to at least two of the electrode segments.

In some examples, the segmented electrode is annular, and wherein each of the electrode segments has an annular sector shape.

In an example, the piezoelectric actuator includes a stack of multiple piezoelectric crystals.

In another example, the piezoelectric actuator includes multiple sector-shaped piezoelectric crystals attached to one another, and each of the electrode segments is attached to a respective one of the sector-shaped piezoelectric crystals.

There is additionally provided, in accordance with another example of the present disclosure, a phacoemulsification method including inserting a phacoemulsification probe into a lens capsule of an eye, the probe including (i)

a piezoelectric actuator, (ii) a segmented electrode, including multiple electrode segments attached to respective angular sections of a face of the piezoelectric actuator, (iii) a common ground electrode attached to the piezoelectric actuator, and (iv) a needle configured to be inserted into a lens capsule of an eye and to be vibrated by the piezoelectric actuator. Using one or more signal generators, the piezoelectric actuator is vibrated by applying multiple drive signals between the multiple respective electrode segments and the common ground electrode.

The present disclosure will be more fully understood from the following detailed description of the examples thereof, taken together with the drawings in which:

BRIEF DESCRIPTION OF THE DRAWINGS

FIG. 3 is a flow chart schematically describing a method for operating the phacoemulsification apparatus of FIG. 1, in accordance with an example of the present disclosure;

FIG. 4 is a pictorial, schematic drawing of a multi-stack piezoelectric disposed with split electrodes that, using the multi-channel piezoelectric drive system of FIG. 2, can be driven using various possible coupling schemes, in accordance with examples of the present disclosure;

DETAILED DESCRIPTION OF EXAMPLES

Overview

Figure 1:
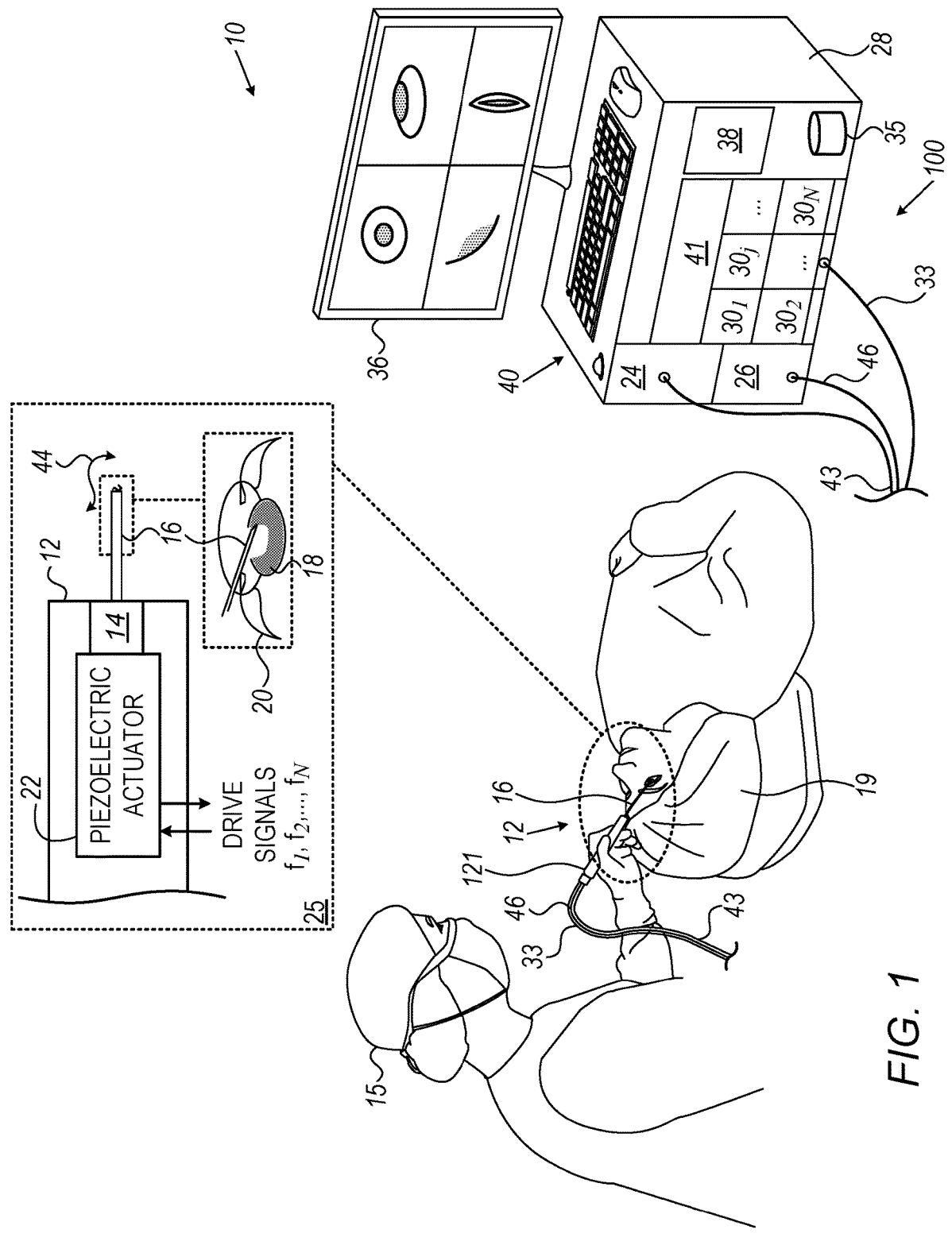
FIG. 1 is a pictorial view, along with a block diagram, of a phacoemulsification apparatus constructed and operating in accordance with an example of the present disclosure.

A phacoemulsification system typically drives a piezoelectric actuator included in a phacoemulsification probe/handpiece to vibrate a needle of the phacoemulsification probe during a cataract procedure. The piezoelectric actuator of the phacoemulsification probe may be designed to vibrate, in resonance, in multiple modes simultaneously, where each mode has a given "natural" resonant frequency. For example, a multi-resonance mode might yield a complex vibration profile that combines longitudinal, transverse, and torsion vibrations, each with its own resonant frequency. Such a mode may have a complex customizable vibration profile that may allow a physician to better perform phacoemulsification.

However, interactions among the different vibration modes of the multi-mode vibration may change their natural frequencies, and the frequencies may further change, for example, as the crystal heats up when it is loaded by ocular media. Thus, it is difficult for the piezoelectric drive system to maintain all of the modes in resonance. The resonant frequency of each of the multiple modes may further depend upon other factors, such as the voltage and current amplitude applied to the piezoelectric actuator, and various other acoustic impedances encountered by the piezoelectric actuator. As a result, complex motion modes, and their potential benefits, may not be practically achievable or maintained for a sufficiently long time.

Moreover, if the resonant frequencies of the piezoelectric actuator change, either due to one of the factors described above, or for any other reason, and further, if the piezoelectric actuator is still powered with signals having the same frequencies (i.e., with part or all of the frequencies being off-resonance), the piezoelectric actuator will heat further. The additional heat may lead to further changes in the resonant frequencies, which in turn may lead to further heat, and so on. Such effects are further complicated because the various resonant frequencies of the piezoelectric actuator typically vary in a non-linear fashion and interact with each other.

Inadequate control of the vibration frequencies can therefore also lead to a hazard as the phacoemulsification needle becomes too hot for the eye. For example, the phacoemulsification needle could reach a temperature of 42° C., above which the proteins in the eye may coagulate, which is very dangerous for the eye. While irrigation may be used to reduce the temperature of the phacoemulsification needle, irrigation presents its own problems. For example, irrigation without carefully matched aspiration can increase internal eye pressure to dangerous levels, whereas too much aspiration can lead to eye collapse. Moreover, irrigation may not be sufficient to adequately cool the phacoemulsification needle.

Examples of the present disclosure that are described hereinafter provide improved methods and systems for driving piezoelectric actuator in phacoemulsification applications. The disclosed techniques facilitate multi-resonant phacoemulsification vibration modes to improve probe efficacy and, at the same time, solve thermal hazard problems. Some examples provide a phacoemulsification apparatus comprising a multi-channel resonant drive system that drives the piezoelectric actuator (e.g., a piezoelectric crystal of the actuator) in a multimode vibration mode by adaptively adjusting each of the frequencies of the drive signals independently of the other frequencies. In this way, the drive system collectively (i.e., using all frequencies simultaneously) drives the piezoelectric actuator while tracking the changing resonant frequencies, thereby maximizing stroke amplitude, enabling a complex motion (e.g., vibration) profile of the needle (e.g., moving in an elliptical track) while minimizing temperature rise of the phacoemulsification probe.

The disclosed examples provide individual processor-controlled drive modules to drive each resonant-frequency mode of vibration while controlling the driving oscillator circuitry comprised in the drive-module to oscillate in resonance with the crystal mode it drives regardless of the aforementioned changes in the mode resonant frequency or in the resonant frequencies of other modes. Each of the separate drive modules may be realized in hardware or software, for example, in a proportional-integral-derivative (PID) control architecture. The different frequencies of the drive signals are adjusted independently of the others and enable vibration of the piezoelectric actuator continuously at the selected multimode resonant mode.

While driving the vibration, the drive modules modify the driving signal frequencies to follow the actuator's varying resonant frequencies by minimizing each frequency with a measured feedback signal, such as a measured phase difference between different voltages across the piezoelectric actuator and respective currents flowing through the piezo-electric actuator in response to the different drive signals. More formally, each module measures a phase difference, $\Delta\phi$, between the driving voltage V and the resulting current I outputted by the driving oscillator and minimize $\Delta\phi$, to maintain the oscillator driving the crystal mode in a reso-nance frequency. Each drive module thus maintains a nomi-nal resonant frequency $f_1, f_2, \ldots, f_N$, and the different drive modules each vary a respective nominal frequency by mini-mizing respective phase difference, $\Delta\phi_j$, j=1, 2 . . . , N, thereby keeping the complex-mode of the crystal in reso-nance.

In an example, the phacoemulsification probe includes a horn, a needle coupled with the horn and configured for insertion into a lens capsule of an eye, and a piezoelectric actuator configured to vibrate the horn and the needle with a multiple-frequency resonant mode. The probe is driven by a multi-channel piezoelectric drive system, having multiple respective resonant drive signal frequencies, the system comprising: (a) multiple respective signal generators con-figured to generate the multiple respective drive signals to drive a vibration of a piezoelectric actuator at the multiple drive signal frequencies of a respectively multiple-fre-quency resonant mode of the piezoelectric actuator, (b) multiple respective phase detection circuitries configured to measure respective multiple phase differences between respective voltages of the drive signals across the piezoelec-tric actuator, and respective electrical currents flowing through the piezoelectric actuator in response to the drive signals delivered at the multiple drive signal frequencies, and (c) a processor configured to independently adjust each drive signal frequency so as to minimize the respective multiple measured phase differences, to maintain the piezo-electric actuator vibrating at the multiple-frequency resonant mode.

In some examples, the multimode piezoelectric crystal comprises a stack of crystals, whereas in other examples, a single crystal is used. The one or more crystals are termi-nated by a uniform or multiple-split electrode (also called hereinafter "segmented electrode"). In an example, each multiple-split electrode is formed of multiple electrode segments attached to respective angular sections of a face of the piezoelectric actuator, and the processor is configured to connect at least two of the drive signals to respective different combinations of the electrode segments. For example, four separate electrode segments may be com-prised in a single electrode to allow the aforementioned multi-channel resonant drive system to vibrate any type of piezoelectric crystal in multiple modes, as described below. In addition, combinations of these modes may be used in synchrony to generate, for example, a final needle motion as the aforementioned elliptical track needle vibration.

By providing a phacoemulsification apparatus that drives multiple electrodes resonantly, and by using multiple drive modules to maintain the multi-resonant mode of motion, improved phacoemulsification may be possible.
System Description FIG. 1 is a pictorial view, including a block diagram, of a phacoemulsification apparatus 10 constructed to operate in accordance with an example of the present disclosure. As seen in the pictorial view of phacoemulsification apparatus 10, and the block diagram in inset 25, it includes a pha-coemulsification probe/handpiece 12 comprising a needle 16 configured for insertion into a lens capsule 18 of an eye 20 of a patient 19 by a physician 15. Needle 16 is mounted on a horn 14 of probe 12, and is shown in inset 25 as a straight needle. However, any suitable needle may be used with the phacoemulsification probe 12, for example, a curved or bent tip needle commercially available from Johnson & Johnson Surgical Vision, Santa Ana, CA, USA.

A piezoelectric actuator 22 is configured to vibrate horn 14 and needle 16 in one or more resonant vibration modes of the combined horn and needle element. The vibration of needle 16 is used to break a cataract into small pieces during the phacoemulsification procedure.

In the shown example, during the phacoemulsification procedure, a pumping sub-system 24 comprised in a console 28 pumps irrigation fluid from an irrigation reservoir to needle 16 to irrigate the eye. The fluid is pumped via a tubing line 43 running from the console 28 to the probe 12. Waste matter (e.g., emulsified parts of the cataract) and eye fluid are aspirated via needle 16 to the collection receptacle by a pumping sub-system 26 also comprised in console 28 and using another tubing line 46 running from probe 12 to console 28.

Console 28 further comprises a multi-channel piezoelec-tric drive system 100 comprising drive-modules $30_1$, $30_2$, . . . $30_N$, each coupled, using electrical wiring running in cable 33, with a stack of piezoelectric crystals of actuator 22. Drive-modules $30_1$, $30_2$, . . . $30_N$, are controlled by a processor 38 and convey phase-controlled driving signals via cable 33 to adjust frequencies of a multi resonance mode of piezoelectric actuator 22. In response, actuator 22 vibrates needle 16, which performs a complex vibrational trajectory 44 comprising, for example, a combination of longitudinal, transverse, and/or torsional vibrations in synchronization one with the other.

Processor 38 (shown in FIG. 2) adjusts the different frequencies $f_1, f_2, \ldots f_N$ of the drive signals to minimize measured phase differences using any suitable method, for example, an optimization algorithm which is not limited to a gradient descent algorithm. An apparatus that can adjust a frequency of a drive signal so as to minimize the measured phase difference, whereby maintaining a piezoelectric actua-tor vibrating at a resonant frequency, is described in U.S. patent application Ser. No. 16/704054, filed Dec. 5, 2019, titled "Phacoemulsification Apparatus," which is assigned to the assignee of the present patent application, which docu-ment is incorporated by reference with a copy provided in the Appendix.

In an example, piezoelectric actuator 22 is disposed with one or more multiple-split electrodes, and processor 38 is configured to connect different combinations of the one or more multiple-split electrodes, using a switching circuitry 41, to at least part of drive-modules $30_1$, $30_2$, . . . $30_N$, so as to vibrate needle 16 in synchrony with one of several possible prespecified trajectories, such as trajectory 44.

Some or all of the functions of processor 38 may be combined in a single physical component or, alternatively, implemented using multiple physical components. These physical components may comprise hard-wired or program-mable devices, or a combination of the two. In some examples, at least some of the functions of processor 38 may be carried out by suitable software stored in a memory 35 (as shown in FIG. 1). This software may be downloaded to a device in electronic form, over a network, for example. Alternatively, or additionally, the software may be stored in tangible, non-transitory computer-readable storage media, such as optical, magnetic, or electronic memory.

Processor 38 may receive user-based commands via a user interface 40, which may include setting a vibration mode and/or frequency of the piezoelectric actuator 22, adjusting the vibration mode and/or frequency of the piezo-electric actuator 22, setting or adjusting a stroke amplitude of the needle 16, and setting or adjusting an irrigation and/or aspiration rate of the pumping sub-system 26. Additionally, or alternatively, processor 38 may receive user-based commands from controls located in handle 121, to, for example, select trajectory 44, or another trajectory, for needle 16.

Processor 38 is further configured to control the aforementioned pumping sub-systems 24 and 26. As seen in FIG. 1, processor 38 may present results of the procedure on a display 36. In an example, user interface 40 and display 36 may be one and the same such as a touch screen graphical user interface.

The apparatus shown in FIG. 1 may include further elements, which are omitted for clarity of presentation. For example, physician 15 typically performs the procedure using a stereo-microscope or magnifying glasses, neither of which are shown. Physician 15 may use other surgical tools in addition to probe 12, which are also not shown to maintain clarity and simplicity of presentation.

Multi-Channel Piezoelectric Resonant System for Phacoemulsification Probe

Figure 2:
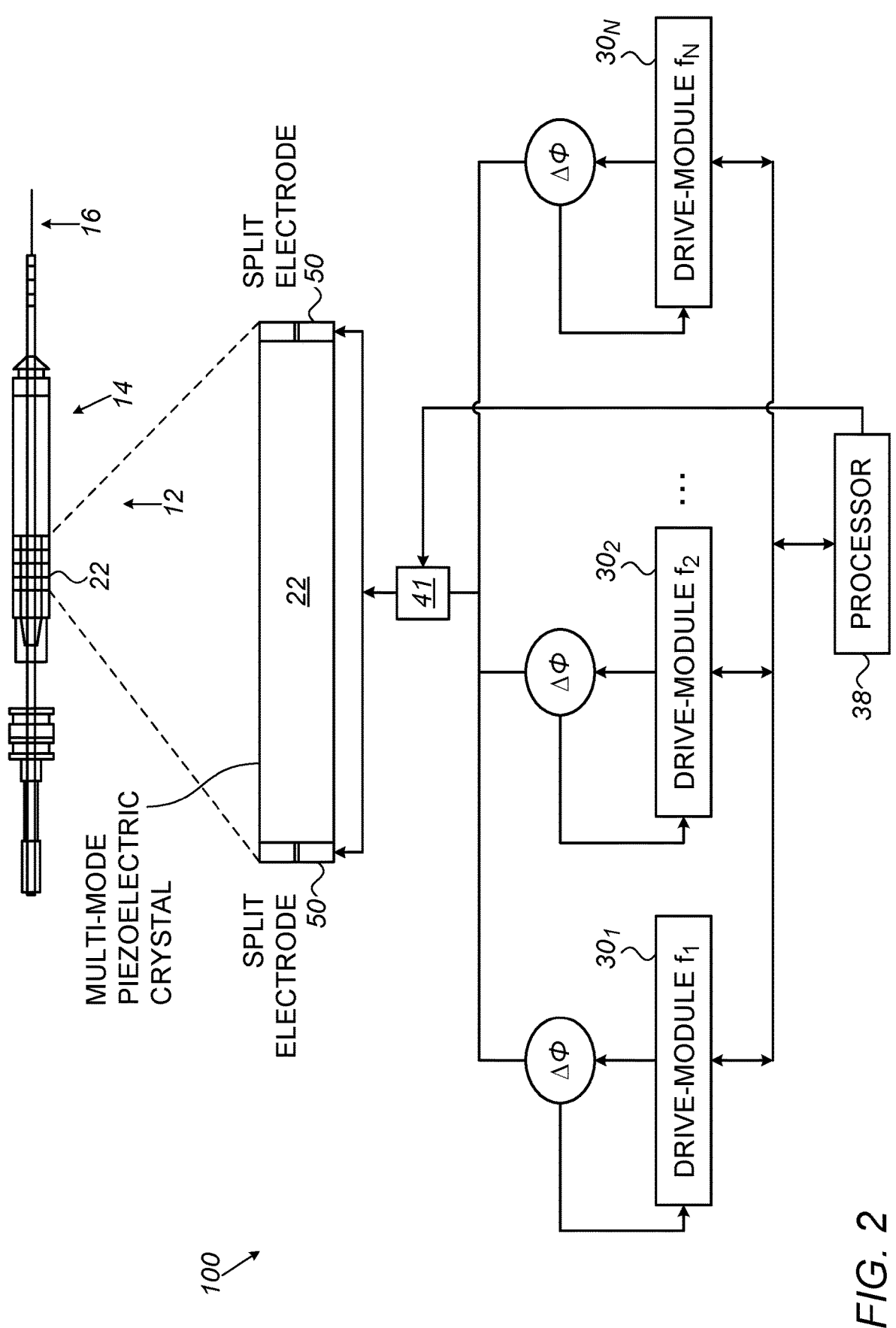
FIG. 2 is a block diagram schematically describing the multi-channel piezoelectric drive system of the phacoemulsification apparatus of FIG. 1, in accordance with an example of the present disclosure.

FIG. 2 is a block diagram schematically describing the multi-channel piezoelectric drive system 100 of phacoemulsification apparatus 10 of FIG. 1, in accordance with an example of the present disclosure.

As seen, drive system 100 comprises drive-modules $30_1$, $30_2$, . . . $30_N$, each coupled to one or more split electrodes 50 of piezoelectric actuator 22 (which may comprise a multi-stack crystal) of phacoemulsification probe 12, using electrical links running in cable 33.

Drive-modules $30_1$, $30_2$, . . . $30_N$, convey driving signals having resonant frequencies $f_1$, $f_2$, . . . $f_N$ of a multi resonance mode of piezoelectric actuator 22 that drive-modules $30_1$, $30_2$, . . . $30_N$, controlled by processor 38, may adjust by minimizing detected respective phase differences, $\Delta\phi_j$, $j$=1, 2 . . . , N, to keep the complex-mode of the crystal in resonance, e.g., following commands from the processor.

Processor 38 is further configured to connect at least part of drive-modules $30_1$, $30_2$, . . . $30_N$, using a switching circuitry 41, with different combinations of the one or more multiple-split electrodes 50 of piezoelectric actuator 22, so as to vibrate needle 16 in synchrony in one of several prespecified trajectories.

The example illustration shown in FIG. 2 is chosen purely for the sake of conceptual clarity. FIG. 2 shows only parts relevant to examples of the present disclosure. Other system elements, such as for eye irrigation, and for removal of debris from the eye, are omitted.

FIG. 3 is a flow chart schematically describing a method for operating phacoemulsification apparatus 10 of FIG. 1, in accordance with an example of the present disclosure. The algorithm, according to the presented example, carries out a process that begins with physician 15 inserting phacoemulsification needle 16 of probe 12 into a lens capsule 18 of an eye 20, at a probe insertion step 102.

Next, physician 15 activates, for example using a control over handle 121 or a foot pedal (not shown), probe 12 to vibrate needle 16 in complex trajectory 44, at a needle vibrating step 104. In response, processor 38 commands a multi-channel piezoelectric drive system 100 to generate signals to drive piezoelectric actuator 22 in the selected multi-resonance vibration mode.

At a needle vibration controlling step 106, drive-modules $30_1$, $30_2$, . . . $30_N$ measure the aforementioned phase differences between voltages and currents across and through piezoelectric actuator 22 (e.g., between split electrodes 50).

Finally, at a needle motion control step 108, system 100 uses the phase information control step 106 to adjust frequencies of the drive signals such that piezoelectric actuator 22 vibrates at the multiple (selected) resonant frequencies, so as to continue vibrating needle 16 in complex trajectory 44.

The example flow chart shown in FIG. 3 is chosen purely for the sake of conceptual clarity. For example, additional steps such as cutting, irrigating, and inspecting the eye are omitted for simplicity and clarity of presentation.

FIG. 4 is a pictorial, schematic drawing of a multi-stack piezoelectric 222, which is assembled by stacking four similar single-crystal piezo elements one on the other. Multi-stack piezoelectric 222 is disposed with split electrodes 50 that, using multi-channel piezoelectric drive system 100 of FIG. 2, can be driven using various possible coupling schemes 55_a-55_e, in accordance with examples of the present disclosure.

As FIG. 4 shows, each of electrodes 55 is split into four electrode segments that receive respective voltages $V_1$-$V_4$ relative to an electrical ground, Gnd, also called hereinafter "common ground."

The 4-split electrodes enable various driving configurations, as follows:

Configuration 55_a, in which all four electrode segments are independently driven by four different voltages, e.g., voltages generated by four respective drive-modules $30_1$-$30_4$ at different (e.g., similar but not necessarily equal) resonant frequencies. By selecting synchronization and amplitude of voltages $V_1$-$V_4$, a complex vibration trajectory, such as a circular trajectory, is possible with configuration 55_a.

Configuration 55b has two electrode segments that are independently driven by two different voltages to vibrate a crystal in one lateral axis, whereas configuration 55_c has two electrode segments independently driven by two different voltages to vibrate the crystal in an orthogonal lateral direction relative that of to 55_b.

Configurations 55_d and 55_e have two electrode segments independently driven by two different voltages to vibrate a crystal in two mutually orthogonal lateral axes that are rotated 45° relative to those of configurations 50_b and 50_c.

The spilt electrodes of FIG. 4 are brought by way of example, and other configurations are possible, such as having six electrode segments, each with a 60° angular section of an electrode 50.

Phacoemulsification Probe Equipped with Piezoelectric Vibrator Comprising Split-Electrode Single-Crystal Stack or Multi-Crystal As noted above, in one example, shown in FIG. 5A below, the needle is vibrated by a piezoelectric vibrator comprising a stack of split-electrode single-crystal elements. In another example, shown in FIG. 5B below, the needle is vibrated a piezoelectric vibrator comprising a multi-crystal element made of angular sections.

Figures 5A, 5B:
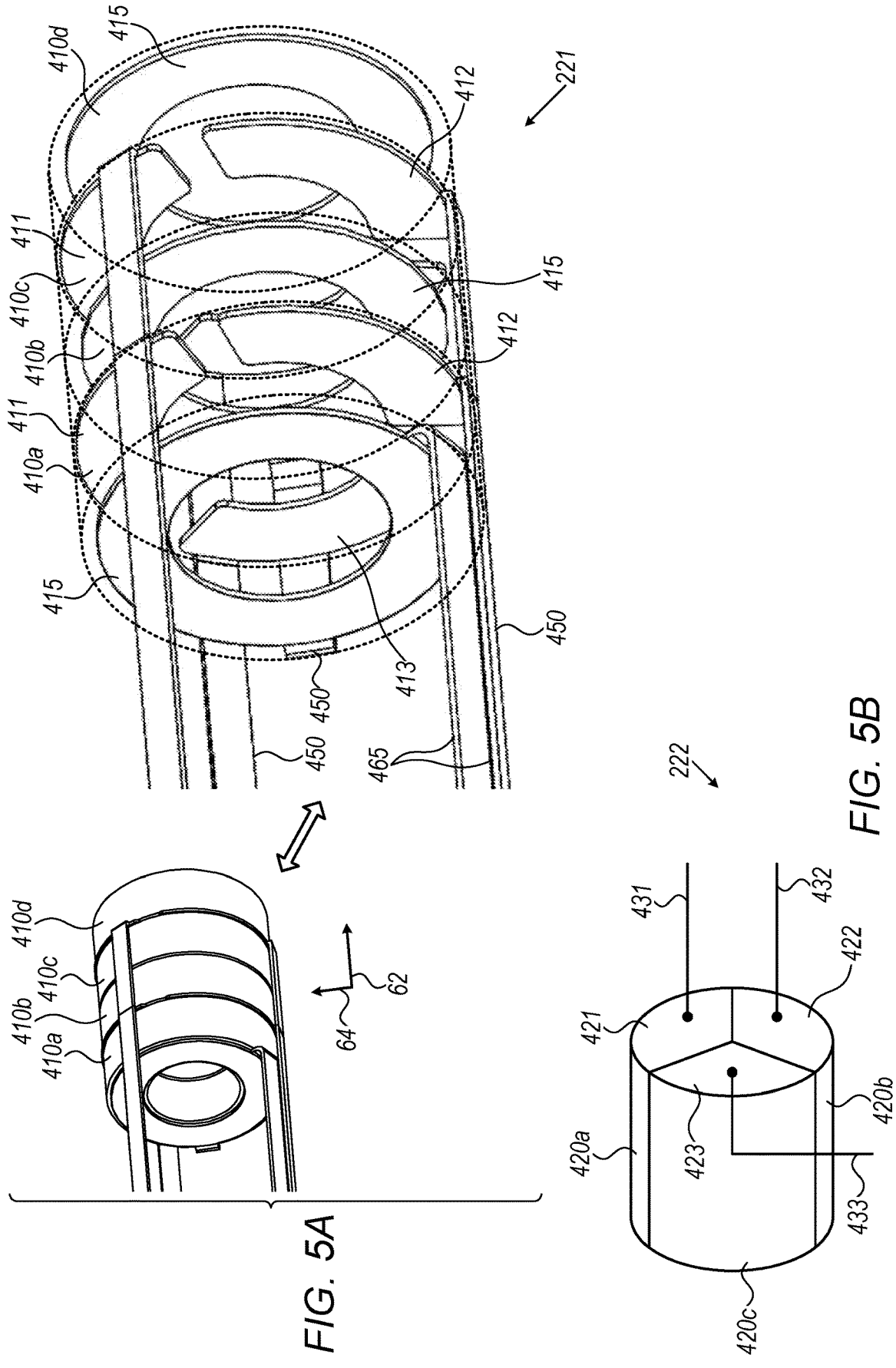
FIGS. 5A and 5B are schematic, pictorial illustrations of a stack of split-electrode single-crystal elements and of a multi-crystal element made of angular crystal sections, respectively, that can be used in the phacoemulsification probe of FIG. 1, in accordance with examples of the present disclosure.

FIGS. 5A and 5B are schematic, pictorial illustrations of a stack 221 of split-electrode single-crystal elements and of a multi-crystal element 222 made of angular crystal sections, respectively, that can be used in phacoemulsification probe 12 of FIG. 1, in accordance with examples of the present disclosure.

As seen in FIG. 5A, split-electrode single-crystal stack 221 is assembled by stacking along longitudinal axis 62 four similar single-crystal piezo elements 410a, 410b, 410c, and 410d, which are angularly aligned. Each of piezo elements 410a, 410b, 410c, and 410d comprises a single-crystal piezo element having an annular cross section. As seen in the larger view on the right-hand side of FIG. 5A, each single-crystal element (with borders shown dotted) is disposed with three electrodes 411, 412 and 413. In a given piezo element (410a, 410b, 410c, or 410d), each of electrodes 411, 412 and 413 is applied to a respective approximately 120° angular section of the piezo element. The segmented electrode is thus annular, and each of the electrode segments has an annular sector shape.

Also shown are electrical leads 450 for driving the different electrodes of the different angular sections. In some examples, processor 38 is configured to drive the various electrodes independently of one another, so as to apply any desired vibration pattern (e.g., a transverse mode of vibration along a transverse plane shown by axis 64). Typically, although not necessarily, processor 38 drives the electrodes of each angular section (across the stack of elements 410a-410d) with the same drive signal.

To drive piezo elements 410a, 410b, 410c, and 410d, each piezo element is disposed with a solid electrode 415 on the opposite side of the piezo element. In an example, the solid electrodes of the different piezo elements are used as an electrical common ground, with electrical leads 465, that may be electrically connected one with the other.

In principle, a single thick crystal could be used instead of a stack. In practice, however, a stack such as stack 410a-410d performs better, and is easier to manufacture. As noted above, single-crystal elements 410a-410d are angularly aligned so that the disposed electrode sections are aligned rotationally to act together. To account for any misalignment during assembly the electrode sections are undersized with respect to the metalized surfaces of the crystal elements. Nevertheless, a calibration can be used for the driving waveforms, to correct any residual angular misalignment. Nevertheless, if the electrode spanned into another metalized region the probe may not perform as desired even using calibration.

Benefits realized the disclosed configuration include:

1) Stacking of multiple single crystals is simpler and achieves better performance than stacking triplets of sector-shaped crystals, e.g., because the top and bottom crystal surfaces are more planar and better aligned.
2) Since each layer of the stack is a single monolithic crystal, there is no need for spacers that may be needed in sector-shaped assemblies.
3) Since each crystal has a well-controlled inner diameter, the risk of placement errors that cause heating is minimized.
4) Since the number of parts in the stack is small, relative to a stack made of triplets of sector-shaped crystals, the assembly process is simple.
5) As the crystals are electrically in parallel with respect to the system, this allows for operation at a lower voltage which makes system and device design easier.

FIG. 5B illustrates an alternative example. In this example, the piezoelectric vibrator comprises multi-crystal element 222 that is made of three angular crystal section elements 420a, 420b and 420c, which are glued together. Angular crystal section elements 420a, 420b and 420c have respective angular section electrodes 421, 422 and 423 disposed thereon. Also shown are respective electrical leads 431, 432 and 433 for driving the different angular section electrodes.

A piezoelectric vibrator comprising a multi-crystal element made of angular sections, such as that of FIG. 5B, is described in U.S. patent application Ser. No. 17/231,450, titled "Compensating for Imperfect Behavior of Multi-Piezoelectric Crystal," Filed Apr. 15, 2021, whose disclosure is incorporated herein by reference.

The examples of piezoelectric vibrator shown in FIGS. 5A and 5B were chosen purely for the sake of conceptual clarity. In general, other configurations may be used, such as, in FIG. 5A, a piezoelectric vibrator made of any two or more number of piezoelectric crystals that are stacked. In FIG. 5B, a piezoelectric vibrator made of any two or more number of piezoelectric crystals are sector-shaped. Thus, the number of angular sections per piezoelectric vibrator may differ from the shown 120-degrees (three sections) example.

Accordingly for FIGS. 5A and 5B, any respective two or more number of electrodes are patterned to energize separately the different piezoelectric crystals.

Additional Electrode Arrangements for Generating Desired Vibration

Figure 6A:
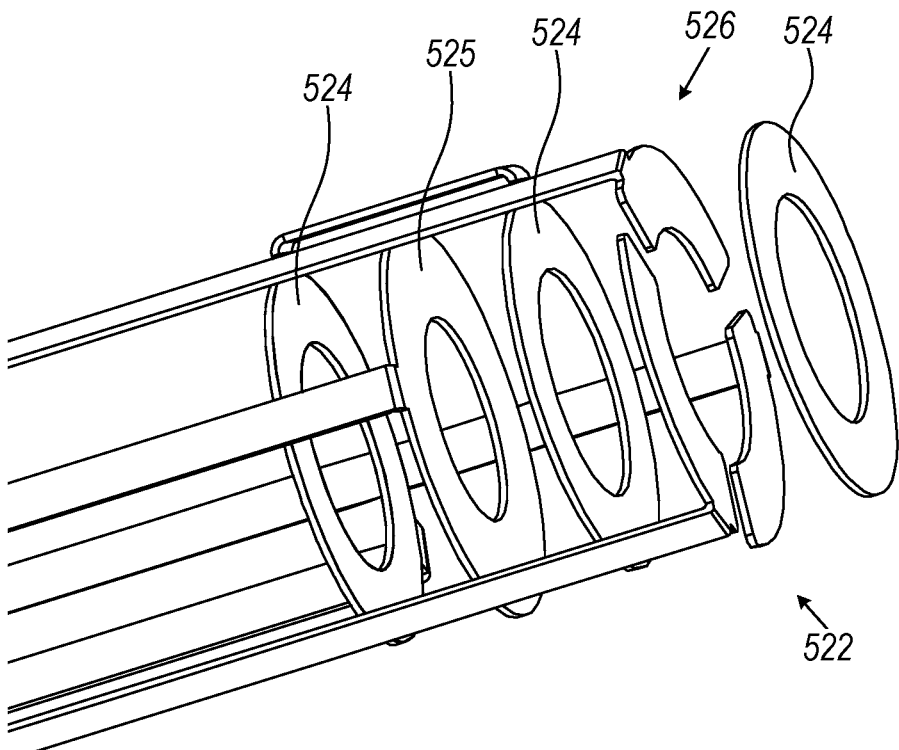
FIGS. 6A and 6B are schematic, pictorial illustrations of a stack of single-crystal elements using either a single split-electrode or two split-electrodes, respectively, in accordance with other examples of the present disclosure.
Figure 6B:
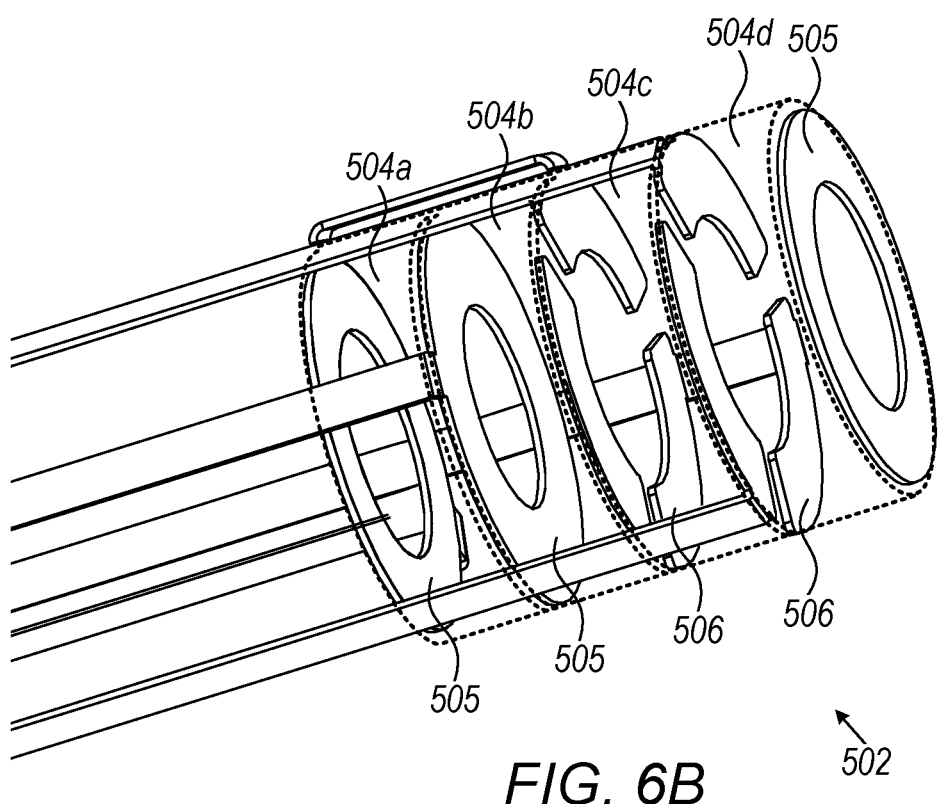

FIGS. 6A and 6B are schematic, pictorial illustrations of stacks 522 and 502 of single-crystal elements using, for driving circular, transverse, helical, and/or rotational motion, either a single split-electrode 526 or two disposed split-electrodes 506, respectively, in accordance with other examples of the present disclosure.

Stacks 522 or 502 can be used, for example, in the phacoemulsification probe of FIG. 1.

In stacks 522 and 502, two crystals (shown in FIG. 6B) are used for inducing a first motion (e.g., longitudinal motion) of the needle. Two other crystals (also shown in FIG. 6B) are used for inducing a second motion (e.g., rotational, transverse, helical, or circular).

In FIG. 6A, of the five electrodes shown, from left to right, electrode serial numbers 1, 3, 5 (i.e., electrodes 524) are connected to electrical ground. The serial number 2 electrode (i.e., electrode 525) is used for driving a first motion or movement (e.g., longitudinal) and serial number 4 electrode (labeled 526) is a split-electrode (split into 3 arcs) used for driving a second motion or movement (e.g., rotational, transverse, helical, or circular) of the needle.

Driving electrodes (524, 525, 524, 526, 524) with respective polarities of (−, +, −, +, −), with − denoting ground, allows floating ground to be applied at the two ends and interface with the horn so the needle and handle are grounded. This solution also simplifies wiring.

FIG. 6B shows piezoelectric crystals 504a-504d. In FIG. 6B, there are three full electrodes 505 using dashed lines. As seen, stack 502 is driven using two split-electrodes 506. Electrodes 506 are made by split metallization, which is typically metalized in a similar manner on both sides of crystal 504c. This configuration is beneficial as the manufacturer of the electrodes can utilize the same mask for both sides. Plating the crystal symmetrically with split-electrodes 506 also aids in assembly, as the rotation of the crystal can be seen from above as each piece is placed onto the horn. One of electrodes 506 may later be wired to ground (e.g., by electrically shortcutting the split electrodes of one of electrodes 506).

Although the examples described herein mainly address phacoemulsification, the methods and systems described herein can also be used in other applications that may require a multi-channel piezoelectric resonant system to drive a moving member.

It will thus be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A phacoemulsification system, comprising:
a phacoemulsification probe, comprising:
    a piezoelectric actuator;
    a segmented electrode, comprising multiple electrode segments attached to respective angular sections of a face of the piezoelectric actuator;
    a common ground electrode attached to the piezoelectric actuator; and
    a needle configured to be inserted into a lens capsule of an eye and to be vibrated by the piezoelectric actuator;
    a plurality of respective signal generators, configured to vibrate the piezoelectric actuator by applying respective drive signals between each of the multiple respective electrode segments and the common ground electrode and to measure respective phase differences between a respective voltage of each respective drive signal and a respective current of each respective drive signal; and
    a controller configured to individually adjust respective frequencies of each of the respective drive signals based on the respective measured phase differences between the voltage of each respective drive signal and the current of each respective drive signal.

2. The system according to claim 1, wherein the multiple drive signals applied between the multiple electrode segments and the common ground electrode each have all of the same signal characteristics.

3. The system according to claim 1, wherein the multiple drive signals applied between the multiple electrode segments and the common ground electrode each have at least one different characteristic.

4. The system according to claim 1, wherein the segmented electrode is annular, and wherein each of the multiple electrode segments has an annular sector shape.

5. The system according to claim 1, wherein the piezoelectric actuator comprises a stack of multiple piezoelectric crystals.

6. The system according to claim 1, wherein the piezoelectric actuator comprises multiple sector-shaped piezo-electric crystals attached to one another, and wherein each of the multiple electrode segments is attached to a respective one of the sector-shaped piezoelectric crystals.

7. A phacoemulsification method, comprising:
inserting a phacoemulsification probe into a lens capsule of an eye, the probe comprising:
    a piezoelectric actuator;
    a segmented electrode, comprising multiple electrode segments attached to respective angular sections of a face of the piezoelectric actuator;
    a common ground electrode attached to the piezoelectric actuator; and a needle, which is configured to be vibrated by the piezoelectric actuator; and
using a plurality of respective signal generators, vibrating the piezoelectric actuator by applying multiple respective drive signals between each of the multiple respective electrode segments and the common ground electrode and to measure respective phase differences between a respective voltage of each respective drive signal and a respective current of each respective drive signal; and
a controller configured to individually adjust respective frequencies of each of the respective drive signals based on the respective measured phase differences between the voltage of each respective drive signal and the current of each respective drive signal.

8. The method according to claim 7, wherein the multiple drive signals applied between the multiple electrode segments and the common ground electrode each have all of the same signal characteristics.

9. The method according to claim 7, wherein the multiple drive signals applied between the multiple electrode segments and the common ground electrode each have at least one different characteristic.

10. The method according to claim 7, wherein the segmented electrode is annular, and wherein each of the electrode segments has an annular sector shape.

11. The method according to claim 7, wherein the piezoelectric actuator comprises a stack of multiple piezoelectric crystals.

12. The method according to claim 7, wherein the piezoelectric actuator comprises multiple sector-shaped piezoelectric crystals attached to one another, and wherein each of the electrode segments is attached to a respective one of the sector-shaped piezoelectric crystals.

* * * * *